United States Patent [19]

Kuber

[11] Patent Number: 5,217,475
[45] Date of Patent: Jun. 8, 1993

[54] TONGUE SCRAPERS

[76] Inventor: Deepty U. Kuber, 2906 Whittington Pl., Tampa, Fla. 33618

[21] Appl. No.: 785,762
[22] Filed: Oct. 31, 1991
[51] Int. Cl.⁵ .............................................. A47L 13/12
[52] U.S. Cl. ...................................... 606/161; 15/111
[58] Field of Search ........................... 606/161; 15/111

[56] References Cited

U.S. PATENT DOCUMENTS

| 1,893,524 | 5/1932 | Shanley | 606/161 |
| 2,574,654 | 11/1951 | Moore | 606/161 |
| 3,995,345 | 12/1976 | Larsson | 15/111 |
| 5,020,181 | 6/1991 | Leonard | 15/111 |

FOREIGN PATENT DOCUMENTS

| 0399946 | 7/1909 | France | 606/161 |
| 2568465 | 2/1986 | France | 606/161 |
| 0793361 | 4/1958 | United Kingdom | 15/111 |

Primary Examiner—Edgar S. Burr
Assistant Examiner—Anthony H. Nguyen
Attorney, Agent, or Firm—Dominik, Stein, Saccocio, Reese, Colitz & Van Der Wall

[57] ABSTRACT

A normally planar tongue scraper. The scraper has free ends and a central extent therebetween. The central extent has a first edge and a second edge with one of the edges having teeth formed therein. The teeth are undulating in configuration with arcuate exterior tips adapted to scrape the tongue of a user. The scraper is formed of a flexible material to allow bending along the length during use thereof. In an alternate embodiment, a support device is employed for removeably retaining the ends of the scraper with the central extent in an arcuate configuration. The support device has a handle end and forwardly projecting spaced fingers with slots therein of a size to receive the ends of the scraper.

11 Claims, 2 Drawing Sheets

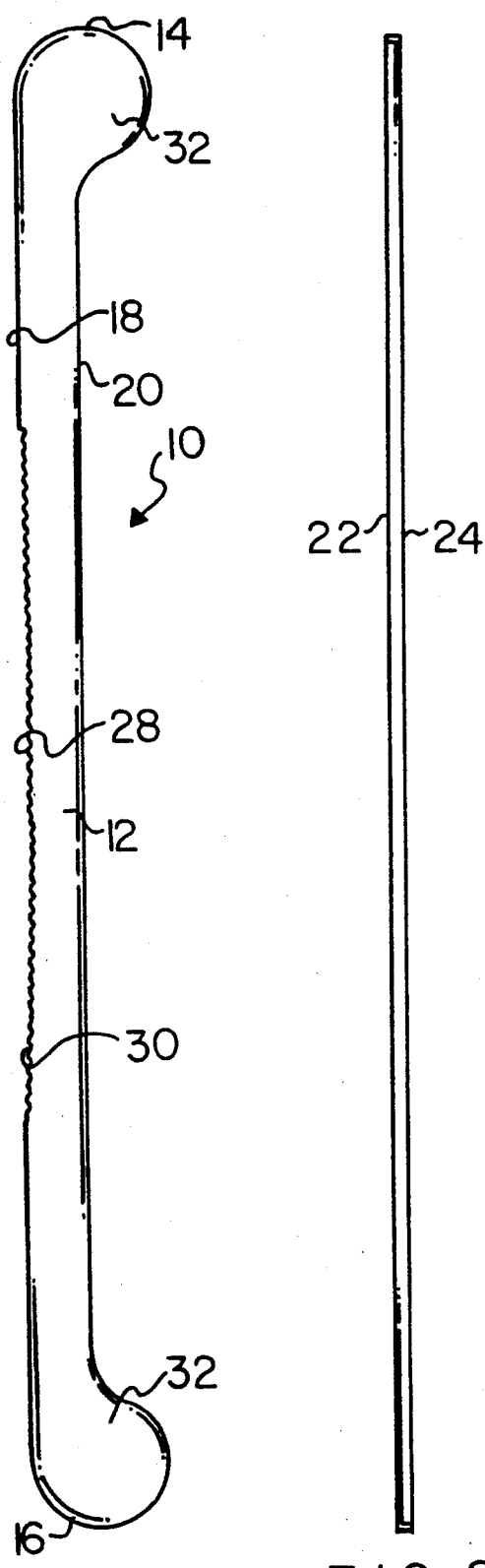
FIG. 1
FIG. 2
FIG. 3
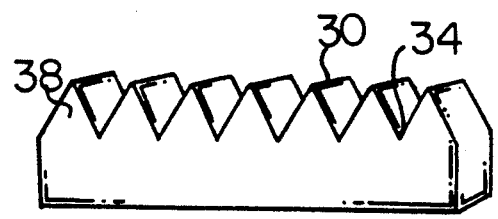
FIG. 4
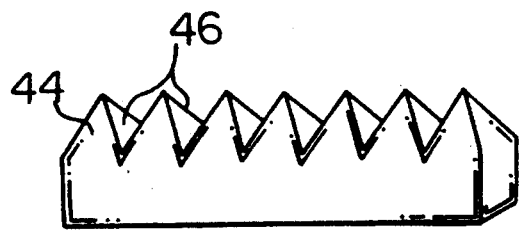
FIG. 5

TONGUE SCRAPERS

BACKGROUND OF THE INVENTION

1. Field of the Invention

The present invention relates to tongue scrapers and, more particularly, to a tongue scraper fabricated of a material to render it disposable for greater sanitation, formed with a serrated edge to improve efficiency, and also including a flavoring and/or fragrance to promote its usage.

2. Description of the Background Art

The United States is a nation, like many others, whose people spend many millions of dollars each year on mouth rinse, breath mints, gum, and like products to freshen the mouth and take bad breath away. One of the simplest methods to achieve this freshening, tongue scraping, has unfortunately long been ignored. Instead of covering up offensive breath odors, efforts should be directed to removing from the mouth the primary cause of such offensive odors. In support of such approach, it has been found that tongue scraping reduces mouth odor by about 75 percent; brushing teeth reduces mouth odor by about 25 percent and scraping the tongue and brushing the teeth reduces mouth odor by 85 about percent.

Mouth odors are caused by dead cells in the mouth, old foods and microorganisms such as bacteria, either alive or dead. These things remain in the mouth, and unless removed, will mix with saliva to form plaque, a white slimy substance. Plaque not only causes bad breath, but is also harmful to the teeth and gums.

The tongue is an important sensory organ. It is also a haven for the microorganisms that cause offensive odors. It is also a haven for those things that attack the teeth and gums. Daily tongue cleaning through scraping significantly reduces plaque-coating bacteria without causing any deleterious tissue changes in the tongue. Tongue cleaning reduces the amount of coating on the tongue by more than about 40 percent. Tongue cleaning inhibits plaque formation on the teeth by about 33 percent. Tongue cleaning will cut down the bacteria stored in the mouth tenfold. The tongue should be cleaned at least twice daily.

The physiology and anatomy of the tongue is such that it becomes a haven for the germs. The physiology of the tongue is slightly furry in texture and has numerous projections, i.e., papillae, that becomes a breading ground for bacteria to grow which allows greater opportunity for the collection of germs, food debris, dead cells and microorganisms, alive or dead. Over time, some collected material, which becomes a soft plaque, makes up a firm attachment to the teeth and gums. Elimination of plaque from the surface of the tongue, therefore, is important for overall mouth cleaning and hygiene.

The present invention eliminates offensive odor in the mouth, functions to obtain and maintain adequate, home oral hygiene, and abates some periodontal diseases. The culprit in periodontal diseases is plaque. The best defense in adequate oral hygiene in today's society is getting rid of the bacteria which causes plaque from all surfaces of the mouth where they breed freely and multiply.

The background art discloses many types of tongue scrapers. By way of example, U.S. Pat. No. 3,477,435 to Artelli discloses a tongue scraper with a metal blade-like member having one end portion formed to fit between wooden handle parts. An essentially rigid blade-like portion extends forwardly of the handle at the other end in a curve for a right-handed or lefthanded person.

U.S. Pat. No. 3,890,964 to Castanedo discloses a one-piece tongue scraper which includes an elongated handle at one end with longitudinally diverging arms at the other end. The ends of the arms are interconnected by a longitudinally bowed cross bar. The cross bar has a laterally centered arched portion and bevelled edge faces.

Lastly, U.S. Pat. No. 4,455,704 to Williams discloses a toothbrush in combination with a tongue cleaner. The tongue cleaner is an arcuate scraper member which is centrally secured to the tooth brush handle at the end opposite the brush.

Other utility patents of interest include U.S. Pat. No. 194,364 to Morganthau; 697,336 to Hagerty; 1,701,616 to Gross; 1,728,956 to Darmitzei; 1,741,143 to Chin; 1,811,775 to Barkwill; 2,405,029 to Gallanty; 2,574,654 to Moore; 2,583,750 to Runnels; 2,651,068 to Seko; and 3,811,447 to Weber.

In addition, U.S. design patents of interest include DES. 221,036 to Potti; 238,108 to Cooke; 242,744 to Rendleman; 246,878 to Kitzis; 253,789 and 287,508 to Gupta; 258,111 to Christen; 259,209 and 286,326 to Gautama; 265,270 to McCarty; 265,506 to Finamore; 281,720 to Tiwari; 283,952 to Berkowitz; 285,250; 285,251; 285,252; 285,253; 285,341; and 285,342 to Audette; and 299,055 and 303,289 to Swamy.

The background art discloses a wide variety of tongue scrapers designed to perform in a wide variety of manners. They are fabricated of a wide variety of materials, natural and synthetic, and are designed to a wide variety of shapes and constructions. No background art, however, discloses, teaches or suggests a tongue scraper which is designed to be disposable for one time use and greater hygiene, which is provided with a serrated edge to fit into the dorsal of the tongue for improved efficiency, and which is flavored to enhance its use. All previous tongue scrapers are simply lacking in one regard or another. The construction and curvature of this tongue scraper promotes a visual impact of what and how much comes out by using it.

As illustrated by the quantity of background art, efforts are continuously being made in an attempt to improve tongue scrapers. No prior effort, however, suggests the present invention configured as disclosed herein. Prior tongue scrapers do not provide the benefits realized with the present invention. The present invention achieves its unique purposes, objects and advantages over the prior art through a new, useful and unobvious combination of features, through the utilization of readily available materials and conventional components and at a reduced cost to manufacture.

It is therefore an object of the present invention to provide a tongue scraper formed of a flexible material, the scraper having a first edge and a second edge with one of the edges having with teeth along the central extent thereof.

It is a further object of the present invention to remove thick, coating-like, white and sticky patches of aerobic microflora from the tongue and mouth.

It is a further object of the present invention to freshen the breath by eliminating the odor causing plaque coating from the mouth.

It is a further object of the present invention to improve the taste of food by removing a coating from the surface of the tongue to expose various taste buds.

It is a further object of the present invention to have a scraper with a unique curvature which covers the whole tongue and eases the cleaning action even from the depressed area of the tongue.

It is a further object of the present invention to make tongue cleaners more hygienically clean and safe by making scrapers disposable.

It is a further object of the present invention to make tongue scrapers with flavoring or fragrance to make them more pleasant to the sensory glands and buds and leave freshness in the mouth for longer periods.

It is a further object of the present invention to have a feeling of total cleanliness after its use for physical and emotional oral gratification.

It is a further object of the present invention to be a most convenient, easy and effective instrument or device for oral hygiene daily program for use in today's society.

It is a further object of the present invention to show instantly actual plaque formation on the tongue by using this curvatured, serrated device which leaves a visual impact in the mind.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiments in addition to the scope of the invention defined by the claims taken in conjunction with the accompanying drawings.

SUMMARY OF THE INVENTION

The invention is defined by the appended claims with the specific preferred embodiment shown in the attached drawings. For the purpose of summarizing the invention, the invention may be incorporated into a tongue scraper formed of a flexible material, the scraper having a first edge and a second edge with one of the edges having with teeth along the central extent thereof.

The tongue scraper may be formed of plastic, wood or laminated paper. The tongue scraper teeth may be arcuate and undulating, triangular in shape, or shaped as pyramids. The tongue scraper ends are enlarged and are devoid of teeth. The tongue scraper further includes a flavoring associated with the scraper or a fragrance. The tongue scraper further includes a flavoring integrated with the plastic of the scraper.

The invention may also be incorporated into a system for cleaning the tongue comprising a scraper formed of a flexible material with ends and with teeth formed in one edge between the ends; and a support device for removeably retaining the ends of the scraper, the support device having a handle end and forwardly projecting spaced fingers with slots therein of a size to receive the ends of the scraper.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is an elevational view of the primary embodiment of a tongue scraper constructed in accordance with the principles of the present invention.

FIG. 2 is a planar view of the tongue scraper of FIG. 1.

FIG. 3 is an enlarged perspective showing of the teeth of the device of FIG. 1. FIGS. 4 and 5 are enlarged perspective showings of teeth constructed in accordance with alternate embodiments of the invention.

Similar reference characters refer to similar parts throughout the several views of the drawings.

DETAILED DESCRIPTION OF THE INVENTION

Figure 6:
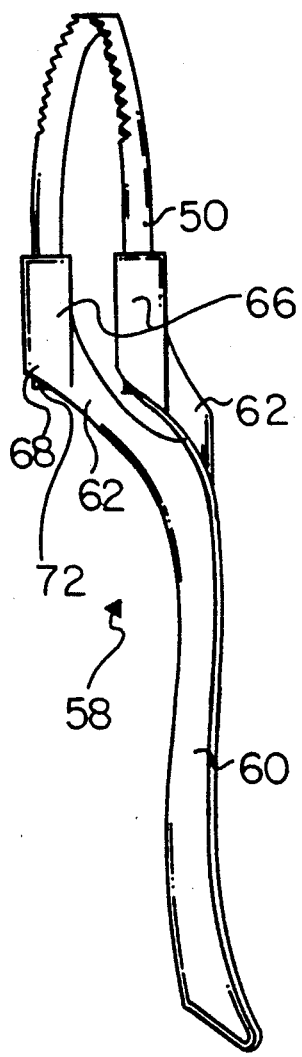
FIG. 6 is a perspective illustration of an alternate embodiment of a tongue scraper constructed in accordance with the principles of the present invention.

Shown in FIG. 1 is the preferred embodiment of a tongue scraper 10 constructed in accordance with principles of the present invention. The scraper has an elongated central extent 12. It has a length of about 9 inches from end 14 to end 16, a width of about ¾ inch from edge 18 to edge 20, and a thickness of about ⅛ inch from face 22 to face 24. A range of about 10 percent of these dimensions is acceptable. In total, the size and construction of the tongue scraper is such that it may be held at its ends 14 and 16 by a user, with one end in each hand, while its central extent 12 may form a smooth curving bend. Note FIGS. 6 and 7. In this manner, the scraper may be inserted into the mouth with its operative edge 18 in contact with the user's tongue, not shown. It may then be pulled across the tongue for scraping the harmful materials therefrom. It is preferred that the scraper be pulled across the tongue at least twice with cleaning of the scraper between such pullings.

The preferred materials of the scraper are either polypropylene or polyethylene. Other types of synthetic, high density polymer plastics which are FDA approved for consumer protection are also acceptable. Typical of yet other acceptable materials include wood and laminated paper. The material should be sufficiently flexible to bend into an arcuate configuration as shown in FIG. 6 upon the application of forces of a user holding the opposite ends. It should be sufficient resilient to return to its linear shape after use and removal of such forces. It should also be sufficiently rigid, however, so that it will retain a linear shape in cross section during use.

The first edge 18 of the scraper 10 is formed over the majority of its length with serrations or teeth 28. The teeth 28 are shown as a plurality of arcuate undulations, wavy lines in the preferred embodiment of FIGS. 1-3. Each tooth 28 extends essentially to a tip or high point 30. When a nine inch scraper is used, the middle six inches are provided with teeth 28, leaving two inches at the opposite ends for handles 32 to be held and controlled by the user. Such handles are enlargements integral with the central extent 12 and project in a direction away from the first edge 18 and teeth 28. The teeth 28 are preferably about sixty to seventy in number. This constitutes about 12-16 teeth per inch. The tips 30 are laterally disposed between about 0.06 and 0.07 inches from each next adjacent tip. From the outermost tip of each tooth to the base 34 between the tips, each tooth 28 is between about 0.06 and 0.07 inches in height. This configuration, size and shape, has been shown to be effective for providing a healthy cleaning and massage to the tongue without damaging any portions thereof. It is also of maximum efficiency in removing essentially all of the contaminants from the tongue.

FIG. 3 is an enlargement of the teeth of FIGS. 1 and 2. FIGS. 4 and 5 are also enlarged showings of teeth constructed in accordance with alternate embodiments of the invention. In the FIG. 4 embodiment, the teeth 38 are not simply wavy lines, but they are formed as triangles of a size and spacing essentially the same as those of FIG. 3.

In the FIG. 5 embodiment, the teeth 44 are formed as pyramids 3. They are beveled, and come to a point at their out board ends or tips. Their faces 46 form triangles between their teeth.

Figure 7:
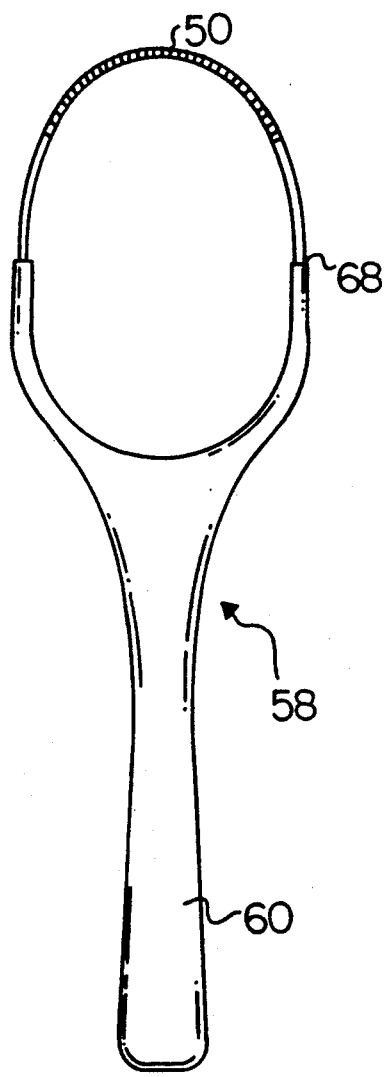
FIGS. 7 and 8 are a plan view and an elevational view of the tongue scraper of FIG. 6.
Figure 8:

Shown in FIGS. 6 through 8 are illustrations of an alternate embodiment of the invention. In such embodiment, the scraper 50 itself is substantially the same as that in the primary embodiment as described above. The only significant difference is that the entire scraper is of a common width from edge 52 to edge 54. This alternate embodiment does not include the end enlargements 32 of the prior embodiments for being held by the user. The scraper 50 is thus adapted to be supported at its ends by a tongue scraper support device 58.

The tongue scraper support device 58 includes a handle portion 60 contoured for convenient holding by the user through the use of only one hand. Its forward end 60 includes two laterally separated fingers 62 extending oppositely from the central handle portion 64. The ends of the fingers are formed with depending supports 66. Such supports have vertical slots 68 of a size for receiving the ends 72 of the scraper 50. With regard to the scraper 50 of the embodiment of FIGS. 6 and 7, the teeth thereof may be of any configuration as for example those described with respect to FIGS. 3, 4, and 5.

When a person is using this tongue scraper 50 and support device 58, a pure linear scraping force would tend to pull the scraper 50 from the slots 68 of the handle portion 60. Such would be an undesirable separation of the two parts of the system. Such separation, however, does not occur during use since the user will be moving the scraper 50 into contact with the tongue while urging the adjacent end of the handle portion 60 downwardly. This will cause the vertical slots 68 of the handle portion 60 to assume a slight angle with respect to the ends 72 of the scraper 50 which they are holding. This angle results in a frictional coupling between the ends 72 of the scraper 50 and the vertical slots 68 in which they are received during operation and use. Consequently, during use, the scraper 50 will remain secured to the handle portion 60. When not in use, the scraper 50 can be easily moved into or out of the slots of the handle portion 60 with a pure linear motion.

In order to encourage usage, the scraper of either of the disclosed embodiments is also provided with a flavoring, artificial or natural. The flavoring is preferably included with the plastic prior to fabrication. Typical flavorings and their combination with plastics are well documented in the literature and are commercially available. Such flavorings may also be added after fabrication of the scraper through a coating or by a powdering as an alternate to flavorings, the scrapers may be provided with fragrances. Fragrances may be added to scrapers in much the same manner as flavorings as described above.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of structures and the combination and arrangement of parts may be resorted to without departing from the spirit and scope of the invention.

Now that the invention has been described, what is claimed is:

1. A normally planar tongue scraper, the scraper having free ends and a central extent therebetween, the central extent having a first edge and a second edge with one of the edges having teeth formed therein along a central portion of the central extent, the scraper having smooth generally parallel edges between the central portion and the free ends, the teeth being undulating in configuration with arcuate exterior tips adapted to scrape the tongue of a user and arcuate valleys between the arcuate exterior tips, the scraper being formed of a flexible material to allow bending along its length during use thereof from a position in which the scraper is planar to a position in which it is "U" shaped.

2. The tongue scraper as set forth in claim 1 wherein the scraper is formed of plastic.

3. The tongue scraper as set forth in claim 1 wherein the tongue scraper is formed of wood.

4. The tongue scraper as set forth in claim 1 wherein the scraper is formed of laminated paper.

5. The tongue scraper as set forth in claim 1 wherein the ends are enlarged and are devoid of teeth.

6. The tongue scraper as set forth in claim 1 and further including a flavoring associated with the scraper.

7. The tongue scraper as set forth in claim 1 and further including a fragrance associated with the scraper.

8. The tongue scraper as set for in claim 2 and further including a flavoring integrated with the plastic of the scraper.

9. The tongue scraper as set forth in claim 1 wherein the teeth are spaced apart from between about 0.06 and 0.07 inches.

10. The tongue scraper as set forth in claim 1 wherein the teeth are between about 0.06 and 0.07 inches deep.

11. A system for cleaning the tongue comprising:
a normally planar tongue scraper, the scraper having free ends and a central extent therebetween, the central extent having a first edge and a second edge with one of the edges having teeth formed therein, the teeth being undulating in configuration with arcuate exterior tips adapted to scrape the tongue of a user, the scraper being formed of a flexible material to allow bending along the length during use thereof; and a support device for removeably retaining the ends of the scraper with the central extent in an arcuate configuraiton, the support device having a handle end and forwardly projecting spaced fingers with slots therein of a size to receive the ends of the scraper.

* * * * *